US006989376B2

(12) United States Patent
Watkins et al.

(10) Patent No.: US 6,989,376 B2
(45) Date of Patent: Jan. 24, 2006

(54) METHODS FOR INCREASING BLOOD CYTIDINE AND/OR URIDINE LEVELS AND TREATING CYTIDINE-DEPENDENT HUMAN DISEASES

(75) Inventors: Carol Watkins, Cambridge, MA (US); Richard J. Wurtman, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/363,748

(22) Filed: Jul. 30, 1999

(65) Prior Publication Data

US 2002/0028787 A1 Mar. 7, 2002

Related U.S. Application Data

(60) Provisional application No. 60/095,002, filed on Jul. 31, 1998.

(51) Int. Cl.
*A61K 31/70* (2006.01)

(52) U.S. Cl. .............................. 514/50; 514/49; 514/51
(58) Field of Classification Search .................. 514/49, 514/50, 51
See application file for complete search history.

(56) References Cited

U.S. PATENT DOCUMENTS

| 4,960,759 A | | 10/1990 | De Luca et al. ............... 514/50 |
| 5,141,943 A | | 8/1992 | Naguib et al. ............... 514/270 |
| 5,470,838 A | | 11/1995 | von Borstel et al. .......... 514/50 |
| 5,567,689 A | | 10/1996 | Sommadossi et al. ........ 514/50 |
| 5,583,117 A | * | 12/1996 | von Borstel et al. .......... 514/50 |
| 5,723,449 A | | 3/1998 | Sommadossi et al. ........ 514/50 |
| 5,962,459 A | * | 10/1999 | Piazza et al. ................. 514/269 |
| 6,472,378 B2 | * | 10/2002 | von Borstel et al. .......... 514/50 |
| 2003/0114415 A1 | * | 6/2003 | Wurtman et al. .............. 514/51 |

FOREIGN PATENT DOCUMENTS

| EP | 0178267 | * | 4/1986 |
| EP | 0178267 A2 | * | 4/1986 |
| JP | 07/215879 A | * | 8/1995 |
| JP | 7215879 | * | 8/1995 |
| JP | 09/30976 A2 | * | 2/1997 |
| JP | 2001/233776 A2 | * | 8/2001 |
| JP | 2001/233776 A2 | * | 8/2004 |
| RU | 2003332 C1 | | 11/1993 |
| WO | WO 89/03837 A1 | * | 5/1989 |
| WO | 8903837 | * | 5/1989 |
| WO | WO89/03837 A1 | * | 5/1989 |
| WO | 9743899 | * | 11/1997 |
| WO | WO 97/43899 A1 | * | 11/1997 |
| WO | WO97/43899 A1 | * | 11/1997 |
| WO | WO97/45127 A1 | * | 12/1997 |
| WO | 9745127 | * | 12/1997 |
| WO | WO 97/45127 A1 | * | 12/1997 |
| WO | WO 00/50043 A1 | * | 8/2000 |
| WO | WO00/50043 A1 | * | 8/2000 |

OTHER PUBLICATIONS

Page et al., "Developmental Disorder Associated with Increased Cellular Nucleotidase Activity," *Proc. National Academy of Sciences USA*, 94(21), 11601–11606 (Oct. 14, 1997).*

(Continued)

*Primary Examiner*—Thomas C. McKenzie
*Assistant Examiner*—L. E. Crane
(74) *Attorney, Agent, or Firm*—Pearl Cohen Zedek Latzer LLP; Mark Cohen (57) ABSTRACT

Methods of treating certain neurological diseases using exogenous uridine or a uridine source alone as a precursor of endogenous cytidine, particularly in the human brain, are disclosed. Methods are also disclosed wherein exogenous uridine or a uridine source is combined either with drugs increasing uridine availability or with compounds that serve as a source of choline in phospholipid synthesis.

8 Claims, 3 Drawing Sheets

OTHER PUBLICATIONS

Coirault et al., "Uridine 5–Triphosphate in Therapy. I. Cure of Neurogenic Muscular Atrophy," *La Presse Medicale(Fr.)*, 68(29), 1127–1129 (Jun. 11, 1960); *Chemical Abstracts*, 57(7), p. 73, Abstract No. 10485f (Oct. 1, 1962).*

Merlini et al., "Effects of Large Doses of Pyrimidine Nucleosides Cytidine and Uridine in Elderly Patients with Neuropsychological Disturbances Caused by Vascular and Cerebral Metabolic Insufficiency," *Gazzetta Medica Italiana Archivio Scienze Mediche*, 145(6), 379–390 (Jun., 1966); *Biological Abtracts*, 83, Abstract No. 27367 (1987).*

Gallai et al. (I), "Effects of Uridine in the Treatment of Diabetic Neuropathy: An Electrophysiological Study," *Acta Neurol. Scand.*, 86(1), 3–7 (1992); *Biological Abtracts*, 94, Abstract No. 112030 (1992).*

Gallai et al. (II), "Multi–Infarct Dementia: Modification of the P300 Cognitive Event–Related Potential in Patients Treated with the Association of Cytidine and Uridine," *Rivista di Neuropsichiatria e Science Affini*, 41(1), 1–9 (1995); *BIOSIS, 1996*, Abstract Citation No. 466219; only Abstract supplied.*

Drago et al., "Memory Deficits of Aged Male Rats Can Be Improved by Pyrimidine Nucleosides and N–Acetylglutamine," *Clinical Neuropharmacology*, 13(4), 290–296 (1990); *Biological Abstracts*, 90, Abstract No. 91117 (1990).*

Manna et al., "Effects of Short–Term Administration of Cytidine, Uridine and L–Glutamine Alone or in Combination on the Cerebral Electrical Activity of Patients with Chronic Cerebrovascular Disease," *Intl. Journal Clinical Pharmacology Research*, 8(3), 199–210 (1988); *Biological Abstracts*, 86, Abstract No. 51989 (1988).*

Keilbaugh et al., "Anti–Human Immunodeficiency Virus Type 1 Therapy and Peripheral Neuropathy: Prevention of 2′, 3′–Dideoxycytidine Toxicity in PC12 Cells, a Neuronal Model, by Uridine and Pyruvate," *Molecular Pharmacology*, 44(4), 702–706 (Oct. 1, 1993); *BIOSIS, 1994*, Abstract Citation No. 413648.*

Popov et al., "Protective Effect of Uridine on D–Galactosamine–Induced Deficiency in Brain Uridine Phosphates," *Biomedica Biochimica Acta*, 43(12), 1399–1404 (1984); *Biological Abstracts*, 80, Abstract No. 34525 (1985).*

Ingraham et al., "Nucleoside Diphosphokinase from *Salmonella typhimurium*," Chapter 48 in *Methods in Enzymology*, LI(vol. 51), Hoffee et al. (eds.), New York, NY, 1978, Academic Press, only pp. 371 and 375 supplied; assorted portions of other chapters were also supplied including pp. 305, 306, 318, 327, 329 and 330.*

Miyazaki et al., "Effects of Nucleotides on Learning and Memory in a Morris Water Maze Test in Normal and Basal Forebrain–Lesioned Rats," *Life Sciences*, 64(1), 45–52 (Nov. 27, 1998).*

Entingh et al., "Brain Uridine Monophosphate: Reduced Incorporation of Uridine During Avoidance Learning," *Brain Research*, 70(1), 131–138 (Apr. 12, 1974); only abstract supplied.*

Rüthrich et al., "Increase of Guanosine Incorporation into RNA of Hippocampal Neurons by Application of Uridine Monophosphate During a Learning Experiments," *Brain Research*, 69(1), 49–55 (Mar. 29, 1974); only abstract supplied.*

Ott et al. (I), "Effects of RNA Precursors on Development and Maintenance of Long–Term Memory," *Psychopharmacologia*, 28(2), 195–204 (*1973*); *Chemical Abstracts*, 78(19), p. 77, Abstr. No. 119731q, (May 14, 1973).*

Ott et al. (II), "Influence of 6–Azauridine on Facilitation of Relearning by Precursors of Ribonucleic Acid," *Psychopharmacologia*, 23(3), 272–278 (*1972*); *Chemical Abstracts*, 76(25), p. 103, Abstr. No. 149588z, (Jun. 19, 1972).*

A. Lehninger, *Biochemistry, Second Edition*, Worth Publishers, Inc., New York, NY, Jul., 1978, only pp. 735–737 supplied.*

Gibbons et al., *Biochemistry of Cholesterol*, Elsevier Biomedical Press, New York , NY, 1982, only pp. 258 and 259 supplied.*

Lodish et al., *Molecular Cell Biology*, W. H. Freeman & Co., New York, NY, 2000, only pp. 68–78 supplied, see especially pp. 75–76.*

Zaffaroni et al., "Adrenal Conversion of $C^{14}$ Labeled Cholesterol and Acetate to Adrenal Cortical Hormones," *Journal of the American Chemical Society*, 73, 1390–1391 (Mar., 1951).*

Kato et al., "Determinants of Sex Hormone Levels in Men as Useful Indices in Hormone–Related Disorders," *Journal of Clinical Epidemiology*, 45(12), 1417–1421 (Dec., 1992).*

(YA) Gibbons et al., Biochemistry of Cholesterol, Elsevier Biomedical Press, New York, NY, 1982, only pp. 258 and 259 supplied.*

(ZA) Lodish et al., Molecular Cell Biology, W. H. Freeman & Co., New York, NY, 2000, only pp. 68–78 supplied, see especially pp. 75–76.*

(RB) Zaffaroni et al., "Adrenal Conversion of C14 Labeled Cholesterol and Acetate to Adrenal Cortical Hormones," Journal of the American Chemical Society, 73, 1390–1391 (Mar., 1951).*

(SB) Kato et al., "Determinants of Sex Hormone Levels in Men as Useful Indices in Hormone–Related Disorders," Journal of Clinical Epidemiology, 45(12), 1417–1421 (Dec., 1992).*

|R| Page et al., "Developmental Disorder Associated with Increased Cellular Nucleotidase Activity," Proc. National Academy of Sciences USA, 94(21), 11601–11606 (Oct. 14, 1997).*

(S) Coirault et al., "Uridine 5–Triphosphate in Therapy. I. Cure of Neurogenic Muscular Atrophy," La Presse Medicale(Fr.), 68(29), 1127–1129 (Jun. 11, 1960); Chemical Abstracts, 57(7), p. 73, Abstract No. 10485f (Oct. 1, 1962).*

(T) Merlini et al., "Effects of Large Doses of Pyrimidine Nucleosides Cytidine and Uridine in Elderly Patients with Neuropsychological Disturbances Caused by Vascular and Cerebral Metabolic Insufficiency," Gazzetta Medica Italiana Archivio Scienze Medic.*

(U) Gallai et al. (I), "Effects of Uridine in the Treatment of Diabetic Neuropathy: An Electrophysiological Study," Acta Neurol. Scand., 86(1), 3–7 (1992); Biological Abtracts, 94, Abstract No. 112030 (1992).*

(V) Gallai et al. (II), "Multi–Infarct Dementia: Modification of the P300 Cognitive Event–Related Potential in Patients Treated with the Association of Cytidine and Uridine," Rivista di Neuropsichiatria e Science Affini, 41(1), 1–9 (1995); BIOSIS, 1996, Ab.*

(W) Drago et al., "Memory Deficits of Aged Male Rats Can Be Improved by Pyrimidine Nucleosides and N-Acetyl-glutamine," Clinical Neuropharmacology, 13(4), 290–296 (1990); Biological Abstracts, 90, Abstract No. 91117 (1990).*

(X) Manna et al., "Effects of Short–Term Administration of Cytidine, Uridine and L–Glutamine Alone or in Combination on the Cerebral Electrical Activity of Patients with Chronic Cerebrovascular Disease," Intl. Journal Clinical Pharmacology Research, 8(3).*

(Y) Keilbaugh et al., "Anti–Human Immunodeficiency Virus Type 1 Therapy and Peripheral Neuropathy: Prevention of 2' 3'Dideoxycytidine Toxicity in PC12 Cells, a Neuronal Model, by Uridine and Pyruvate," Molecular Pharmcology, 44(4), 702–706 (Oct. 1, 19.*

(Z) Popov et al., "Protection Effect of Uridine on D–Galactosamine–Induced Deficiency in Brain Uridine Phosphates," Biomedica Biochimica Acta, 43(12), 1399–1404 (1984); Biological Abstracts, 80, Abstract No. 34525 (1985).*

(RA) Ingraham et al., "Nucleoside Diphosphokinase from *Salmonella typhimurium*," Chapter 48 in Methods in Enzymology, LI(vol. 51), Hoffee et al. (eds.), New York, NY, 1978, Academic Press, only pp. 371 and 375 supplied; assorted portions of other chapter.*

(SA) Miyazaki et al., "Effects of Nucleotides on Learning and Memory in a Morris Water Maze Test in Normal and Basal Forebrain–Lesioned Rats," Life Sciences, 64(1), 45–52 (Nov. 27, 1998).*

(TA) Entingh et al., "Brain Uridine Monophosphate: Reduced Incorporation of Uridine During Avoidance Learning," Brain Research, 70(1), 131–138 (Apr. 12, 1974); only abstract supplied.*

(UA) Ruthrich et al., "Increase of Guanosine Incorporation into RNA of Hippocampal Neurons by Application of Uridine Monophosphate During a Learning Experiments," Brain Research, 69(1), 49–55 (Mar. 29, 1974); only abstract supplied.*

(VA) Ott et al. (I), "Effects of RNA Precursors on Development and Maintenance of Long–Term Memory," Psychopharmacologia, 28(2), 195–204 (1973);Chemical Abstracts, 78(19), p. 77, Abstr. No. 119731q, (May 14, 1973).*

(WA) Ott et al. (II), "Influence of 6–Azauridine on Facilitation of Relearning by Precursors of Ribonucleic Acid, "Psychopharmacologia, 23(3), 272–278 (1972);Chemical Abstracts, 76(25), p. 103, Abstr. No. 149588z, (Jun. 19, 1972).*

(XA) A. Lehninger, Biochemistry, Second Edition, Worth Publishers, Inc., New York, NY, Jul., 1978, only pages 735–737 supplied.*

Page et al., "Developmental Disorder Associated with Increased Cellular Nucleotidase Activity," *Proceedings of the National Academy of Sciences USA*, 94(21), 11601–11606 (Oct. 14, 1997).*

Coirault et al., "Uridine 5–Triphosphate in Therapy. I. Cure of Neurogenic Muscular Atrophy," *Presse Med.(Fr.)*, 68, 1127–1129 (1960); *Chemical Abstracts*, 57(7), p. 73, Abstract No. 10485f (Oct. 1, 1962); only Abstract supplied.*

Merlini et al., "Effects of Large Doses of Pyrimidine Nucleosides Cytidine and Uridine in Elderly Patients with Neuropsycyological Disturbances Caused by Vascular and Cerebral Metabolic Insufficiency," *Gazz. Med. Ital. Arch. Sci. Med.*, 145(6), 379–390 (1966); *Biological Abstracts, 83*, Abstract No. 27367 (1987); only Abstract supplied.*

Gallai et al.(I), "Effects of Uridine in the Treatment of Diabetic Neuropathy An Electrophysiological Study," *Acta Neurol. Scand.*, 86(1), 3–7 (1992); *Biological Abstracts, 94*, Abstract No. 112030 (1992); only Abstract supplied.*

Gallai et al.(II), "Multi–Infarct Dementia: Modification of the P300 Cognitive Event–Related Potential in Patients Treated with the Association of Cytidine and Uridine," *Rivista di Neuropsichiatria e Science Affini*, 41(1), 1–9 (1995); *BIOSIS, 1996*, Abstract Citation No. 466219; only Abstract supplied.*

Drago et al., "Memory Deficits of Aged Male Rats Can Be Improved by Pyrimidine Nucleosides and N–Acetyl-glutamine," *Clinical Neuropharmacology*, 13(4), 290–296 (1990); *Biological Abstracts, 90*, Abstract No. 91117 (1990); only Abstract supplied.*

Manna et al., "Effects of Short–Term Administration of Cytidine, Uridine and L–Glutamine Alone or in Combination on the Cerebral Electrical Activity of Patients with Chronic Cerebrovascular Disease," *Intl. Journal Clinical Pharmacology Research*, 8(3), 199–210 (1988); *Biological Abstracts, 86*, Abstract No. 51989 (1988); only Abstract supplied.*

Keilbaugh et al., "Anti–Human Immunodeficiency Virus Type 1 Therapy and Peripheral Neuropathy: Prevention of 2', 3'–Dideoxycytidine Toxicity in PC12 Cells, a Neuronal Model, by Uridine and Pyruvate," *Molecular Pharmacology*, 44(4), 702–706 (1993); *BIOSIS, 1994*, Abstract Citation No. 413648; only Abstract supplied.*

Popov et al., "Protective Effect of Uridine on D–Galactosamine–Induced Deficiency in Brain Uridine Phosphates," *Biomedica Biochimica Acta*, 43(12), 1399–1404 (1984; rec'd 1985); *Biological Abstracts, 80*, Abstract No. 34525 (1985); only Abstract supplied.*

Connolly et al, Uridine and its nucleotides: biological actions, therapeutic potentials May 1999 20: 218–225.

Camiener, Gerald, "Studies of the Enzymatic Deamination of Cytosine Arabinoside–I"; *Pharmacology*, vol. 14, pp. 1405–1416, 1965.

Cheal, Marylou, "The Gerbil: A Unique Model for Research on Aging", *Experimental Aging Research*, vol. 12, No. 1, pp. 3–11, 1986.

Vincent, Albert L. et al., "The Pathology of the Mongolian Gerbil (*Meriones unguiculatus*): A Review", *Laboratory Animal Science*, pp. 645–651, 1979, (Oct., 1979).

Ross, Brian M. et al., "Phospholipid Biosynthetic Enzymes in Human Brain", *Lipids*, vol. 32, No. 4, 1997.

P.A. Spiers et al., "Citicoline Improves Verbal Memory in Aging", Arch Neurol, 53(5), May 1996, pp. 441–448.

Cornford et al., Independent blood–brain barrier transport systems for nucleic acid precursors. *Biochim. Biophys Acta*, 349:211–219, (1975), (Jun. 25, 1975).

Dawson. Enzymic conversion of uridine nucleotide to cytidine nucleotide by rat brain. *J. Neurochem.*, 15:31–34, (1968), (Jan., 1968).

Becroft DM, et al., Hereditary orotic aciduria: long–term therapy with uridine and a trial of uracil. *J Pediatr.*, 75(5): 885–891, (1969), (Oct., 1969).

Roberts CA, et al., Uridine anticonvulsant effects: selective control of nucleoside incorporation in experimental epilepsy. *Epilepsia*, 15(4): 479–500, (Dec. 1974).

Monticone GF, et al., On the therapeutic use of nucleosides, cytidine and uridine, in some neurological diseases. *Minerva Med.*, 57(101): 4348–4352, (Dec. 19, 1966).

Lopez–Coviella et al., Evidence that 5'–cytidinephosphocholine can affect brain phospholipid composition by increasing choline and cytidine plasma levels. *J. Neurochemistry*, 65: 889–894, (1995), (Aug., 1995).

Ginsburg et al., Rodent models of cerebral ischemia. *Stroke* 20:1627–1642, (1989), (Dec., 1989).

* cited by examiner

FIG.4

METHODS FOR INCREASING BLOOD CYTIDINE AND/OR URIDINE LEVELS AND TREATING CYTIDINE-DEPENDENT HUMAN DISEASES

RELATED APPLICATIONS

This application claims priority to U.S. Provisional Application No. 60/095,002 filed Jul. 31, 1998, which is incorporated herein by reference.

This invention was made with government support under Grant Number NIH-5R37-MH28783 awarded by the National Institute of Health. The government has certain rights in the invention.

BACKGROUND OF THE INVENTION

1. Field of the Invention

The present invention relates to methods of increasing cytidine levels by administering an exogenous uridine source and in particular to the pharmacological use of said uridine or uridine source alone or in combination with other pharmaceutical substances in treating certain neurological disorders.

2. Description of the Related Art

This invention stems from unexpected discovery that increase in levels of uridine following the administration of uridine or uridine source to certain animals comprising human patients, leads to increased levels of cytidine in a human body and particularly in the human brain. Thus, administering uridine or uridine precursors to human patients in need thereof can be as beneficial as administration of cytidine or cytidine precursors. However, the potential benefit of uridine or uridine source administration is overwhelmingly greater than the benefit of cytidine administration. This is due to the fact that cytidine, as opposed to uridine, either cannot cross or is much less efficient than uridine in crossing the blood-brain barrier (Cornford et al., Independent blood-brain barrier transport systems for nucleic acid precursors. *Biochim. Biophys. Acta* 349:211–219, 1975).

According to the knowledge relating to the metabolism of pyrimidine compounds, enzymes are known in the art, such as cytidine deaminase (EC 3.5.4.5), which converts cytidine into uridine. Cytidine deaminase can be found in some prokaryotes and eukaryotes including humans, primates, and some rodents although some species lack this enzyme. However, according to EC (enzyme classification) list there are no known examples of aminase-like enzymes, which are capable of opposite action, i.e., converting uridine into cytidine.

The prior art relating to the process of uridine to cytidine conversion is also limited. Only one publication, citing two earlier references, seems to exist, wherein it was suggested that a soluble fraction of the rat liver and possibly of the brain may catalyze in vitro and in vivo the conversion of uridine nucleotide to cytidine nucleotide (Dawson. Enzymic conversion of uridine nucleotide to cytidine precursor by rat brain. *J. Neurochem.* 15:31–34, 1968). Even though this report implicated the possibility of such an enzyme reaction in rats the activity of the enzyme does not appear to be sufficiently potent. As compared to the initial, administered dose of uridine (considered as 100%), the highest levels of newly converted cytidine in vivo were 12.4% in the liver and 9% in the brain. The conversion rates in vitro were 5.4% in the liver and 8.05% in the brain. Thus, maximum observed levels were within 5.4–12.4% range. From a statistical point of view all these figures are within the range of a typical scatter in a gamma counter (15%) and practitioner in the art can dismiss them either as insignificant or irreproducible. Moreover, Dawson himself states that he was unable to recover a nucleotide with spectrophotometric characteristics of cytidine and admits that his conclusions were based on probabilistic guessing. Thus, the alleged phenomenon observed by Dawson may have been due to misinterpretation of an experimental artifact as it is now known that experimentally measurable cytidine can be easily confused with tyrosine, which is chemically unrelated amino acid compound (see FIG. 1).

Thus, even though an enzyme catalyzing the conversion of uridine to cytidine may exist in rats its activity is not sufficiently potent to raise the levels of cytidine to a level that can be measured and ascertained beyond any doubt. Thus, these levels may be not sufficient to warrant practical exploitation for clinical application. Indeed nowhere in Dawson publication is there a suggestion or an attempt to make a suggestion that the uridine to cytidine conversion process can be useful for any medical modality. In addition, as it is the case with many other enzymes and metabolic pathways, this particular enzyme may have been present in rats but not in humans. One skilled in related art knows that a discovery of a biological process in one species of an animal, e.g., rat, does not necessarily means that a similar process is present in another animal, e.g., man. Based on that one skilled in the art will be not sufficiently motivated to exploit this phenomenon for any useful purposes other than an experimental tool to study enzyme metabolism in rats. Consequently, the prior art is silent in regard to the use of the process of uridine to cytidine conversion for any meaningful application.

Uridine is a pyrimidine nucleoside and is essential in the synthesis of ribonucleic acids and tissue glycogens such as UDP glucose and UTP glucose. Medical uses of uridine alone are limited to treatment of genetic disorders related to deficiencies of pyrimidine synthesis such as orotic aciduria (Becroft D M, et al., Hereditary orotic aciduria: long-term therapy with uridine and a trial of uracil. *J Pediatr.* 1969 November; 75(5): 885–891). Other less common uses of uridine alone are known such as treatment of seizures and epilepsy (Roberts C A, et al., Uridine anticonvulsant effects: selective control of nucleoside incorporation in experimental epilepsy. *Epilepsia.* 1974 December; 15(4): 479–500). Most commonly, uridine is used in combination with cytidine (Monticone G F, et al., On the therapeutic use of the nucleosides, cytidine and uridine, in some neurological diseases. *Minerva Med.* 1966 Dec. 19; 57(101): 4348–4352). The uses of this particular dual combination range from liver and kidney diseases to a number of neurological and cerebrovascular diseases but such uses are irrelevant to the present invention directed at the use of uridine without concomitant use with cytidine.

U.S. Pat. No. 4,960,759, issued to De Luca et al., on Oct. 2, 1990 discloses the pharmacological use of uridine in the treatment of nervous disorders such as schizophrenia and Parkinson's disease. De Luca et al., teach that the benefit of uridine is due to increase in cholecystokinin levels in the brain, which in turn improves dopamine functioning and results in therapeutic benefit. Said benefit is described as a reduction in symptoms of Parkinson's disease, which are tremor and rigidity. As the preferred embodiment of the instant invention is treatment of neurological disorders unrelated to schizophrenia and Parkinson's disease it is clear that the teachings by De Luca et al., are irrelevant to this invention.

The U.S. Pat. No. 5,470,838, issued to von Borstel et al., on Nov. 28, 1995 discloses the method of delivering exogenous uridine or cytidine in form of acylated uridine or cytidine and said compounds as useful in treating cardiac insufficiency, myocardial infarction, and cirrhosis of the liver. Von Borstel et al., propose to use both forms of pyrimidines since it was not obvious to them that uridine alone is effective. The absolute requirement of both cytidine and uridine was due to the lack of knowledge and anticipation in the prior art that uridine might convert into cytidine, especially in humans. One skilled in the art will recognize that the disclosed composition matter is different and diseases to be treated are not the same as in the present invention.

The U.S. Pat. Nos. 5,141,943; 5,567,689; and 5,723,449 disclose various methods and compositions to raise levels of uridine in the blood as useful for reducing toxicity of pyrimidine nucleoside drugs such as AZT and 5-Fluouracil for AIDS and cancer therapy respectively. It is apparent to anyone skilled in the art that these teachings have nothing in common with the present invention.

Although all of these patents and prior art references disclose at least one or another aspect of the instant invention none of them taught specifically that cytidine levels can be raised in humans by administering uridine or uridine source as useful for the treatment of certain neurological or brain disorders. These disorders comprise disorders associated with aging such as memory decline and age related decline in cognition functions. These disorders also comprise memory decline and related cognition dysfunction associated with pathological conditions like Alzheimer's disease, Pick's disease, Lewy Body disease, and/or dementias like Huntington's disease and AIDS dementia. Other cognitive dysfunctions, i.e., disorders of attention, alertness, concentration, focus, and dyslexia can also be treated. Other uses of uridine therapy can be imagined such as treatment of mood and emotional disorders, e.g., mania, depression, stress, panic, anxiety, insomnia, dysthemia, psychosis, seasonal effective disorders and bipolar disorders. Neurological diseases like ataxias, including Friedreich's ataxia and movement disorders like tardive dyskinesia can also be treated. Method of treating stroke, cerebral thrombosis, ischemia, and related cerebrovascular diseases resulting from hypoxia as well as behavioral and neurological syndromes seen after brain trauma, spinal cord injury and/or anoxia can be also imagined. Methods of treating diseases of the peripheral nervous system, e.g., neuromuscular disorders like myasthenia gravis, the post-polio syndrome, and muscular dystrophies are also possible. It is also possible to imagine the methods of treating neurological diseases associated with dopaminergic pathway, e.g., schizophrenia and Parkinson's disease as treated by combination therapy in which uridine is one of constituents.

Thus, none of the prior art patents or references have anticipated or made the instant invention obvious. The present invention is thus unique and stands out in the light of the prior art.

SUMMARY OF THE INVENTION

This invention is based upon the unexpected discovery that uridine administration in humans leads to increases in systemic and brain cytidine. While certain methods of treatment of certain neurological diseases using uridine are known, the prior art has heretofore failed to provide the methods of treatment of diseases which are objects of this invention. These and other objects of the invention will become more readily apparent from the following description.

It is a general object of this invention to provide a novel method of treatment using uridine, uridine prodrugs, and pharmaceutically derivatives thereof alone or in combination with compounds that are useful in increasing uridine availability. The terms "uridine precursor" or "uridine source" or "uridine prodrug" are used interchangeably and as defined hereinafter mean compounds, e.g., uridine salts or food products containing uridine, that transform into uridine upon administration to a host such as human.

The present invention also provides a method of treating various neurological disorders comprising memory disorders associated with aging as well as memory decline and cognitive dysfunction associated with pathological conditions like Alzheimer's disease, Pick's disease, Lewy Body disease, and/or dementias like Huntington's disease and AIDS dementia.

The present invention also provides a method of slowing down or reversing brain-aging process, which may cause memory decline and cognitive dysfunction.

Other uses of uridine therapy are provided such as treatment of cognitive dysfunction, i.e., disorders of attention, alertness, concentration, focus, and dyslexia.

Other uses of uridine therapy are also provided such as treatment of mood and emotional disorders, e.g., mania, depression, stress, panic, anxiety, insomnia, dysthemia, psychosis, seasonal effective disorders and bipolar disorders.

It is also an object of this invention to provide methods for treating other neurological diseases like ataxias, including Friedreich's ataxia.

It is also an object of this invention to provide methods for treating strokes, cerebral thrombosis, ischemia, and related cerebrovascular diseases resulting from hypoxia.

Methods of treating behavioral and neurological syndromes seen after brain trauma, spinal cord injury and/or anoxia are also provided.

The present invention also provides a method of treating patients with movement disorders like tardive dyskinesia.

Methods of treating diseases of the peripheral nervous system, e.g., neuromuscular disorders like myasthenia gravis, the post-polio syndrome, and muscular dystrophies are also provided.

It is also an object of this invention to provide methods for treating other diseases known in the art and involving or dependent on cholinergic or uridine/cytidine metabolic pathways.

Methods of treating neurological diseases associated with dopaminergic pathway, e.g., schizophrenia and Parkinson's disease as treated by combination therapy in which uridine is one of constituents are provided.

In another aspect, the invention provides additional pharmaceutical compositions that can inhibit metabolic degradation or clearance of uridine as compounds enhancing uridine bioavailability. Among such compounds are uridine phosphorylase inhibitors like 5-benzyl barbiturate or derivatives thereof. Among such compounds are also compounds competing with uridine in renal transport mechanism. They comprise compounds like L-uridine, L-2',3'-dideoxyuridine, and D-2',3'-dideoxyuridine. Among such compounds are also uridine secretion inhibiting compounds like dilazep or hexobendine.

Choline is involved in metabolism and lipid transport and is a component of a number of important biological compounds including the membrane phospholipids like lecithin and sphingomyelin. Choline is also a precursor of acetylcholine—one of most important neurotransmitters. Although a required nutrient for several animal species, choline is not currently designated as essential for humans. However, recent clinical studies show it to be essential for normal liver function. Additionally, a large body of evidence from the fields of molecular and cell biology shows that certain phospholipids play a critical role in generating second messengers for cell membrane signal transduction. This process involves a cascade of reactions that translate an external cell stimulus such as a hormone or growth factor into a change in cell transport, metabolism, growth, function, or gene expression. Disruptions in phospholipid metabolism can interfere with this process and may underlie certain disease states such as cancer and Alzheimer's disease. However, choline alone is not useful as a therapeutical modality. In light of the instant invention choline or choline precursors are appropriate in considering them in combination with uridine or uridine source.

It is thus a further object of this invention to establish a synergy between uridine and various compounds affecting cholinergic pathway and/or phospholipid metabolism. Among them are CDP-choline, choline, choline salts, lecithin or phosphatidylcholine, phosphatidylethanolamine, various fatty acids, e.g., linoleic acid, and other known in the art compounds or mixtures thereof involved in phospholipid synthesis.

DESCRIPTION OF THE PREFFERED EMBODIMENTS

The present invention concerns methods and compositions for increasing systemic and brain levels of cytidine in a human patient via administration of uridine or uridine source alone. Also methods and compositions are contemplated which encompass the use of uridine or uridine source in combination with drugs that increase uridine availability. Among such drugs are drugs that act as uridine phosphorylase inhibitors like benzyl barbiturate or derivatives thereof. Among such drugs are also drugs that act as uridine secretion inhibiting compounds like dilazep or hexobendine. Among such drugs are drugs that act as uridine renal transport competitors like L-uridine, L-2',3'-dideoxyuridine, and D-2',3'-dideoxyuridine. Also methods and compositions are disclosed that are beneficial to a human patient in need thereof and which act in synergy with uridine in generation of phospholipids involved in brain cell membrane formation and repair. More specifically choline-based compounds are contemplated as compounds acting in synergy with uridine or uridine source. Among them are choline, choline salts or esters, such as choline bitartrate or stearate or the like, or compound that dissociate to choline, such as sphingomyelin, cytidine-diphospho-choline or citicoline or CDP-choline, acylglycerophosphocholines, e.g., lecithin, lysolecithin, glycerophosphatidylcholine, mixtures thereof or the like.

Neurological diseases associated with dopaminergic pathway, e.g., schizophrenia and Parkinson's disease as treated by uridine alone are specifically excluded.

Other neurological conditions that were suggested to be treatable by uridine like epilepsy, seizures, and convulsions are excluded.

Specific medical uses of uridine in combination with cytidine known in the prior art are also excluded.

The following examples illustrate the invention and are not intended to be limiting unless otherwise specified.

EXAMPLE 1

Figure 1:
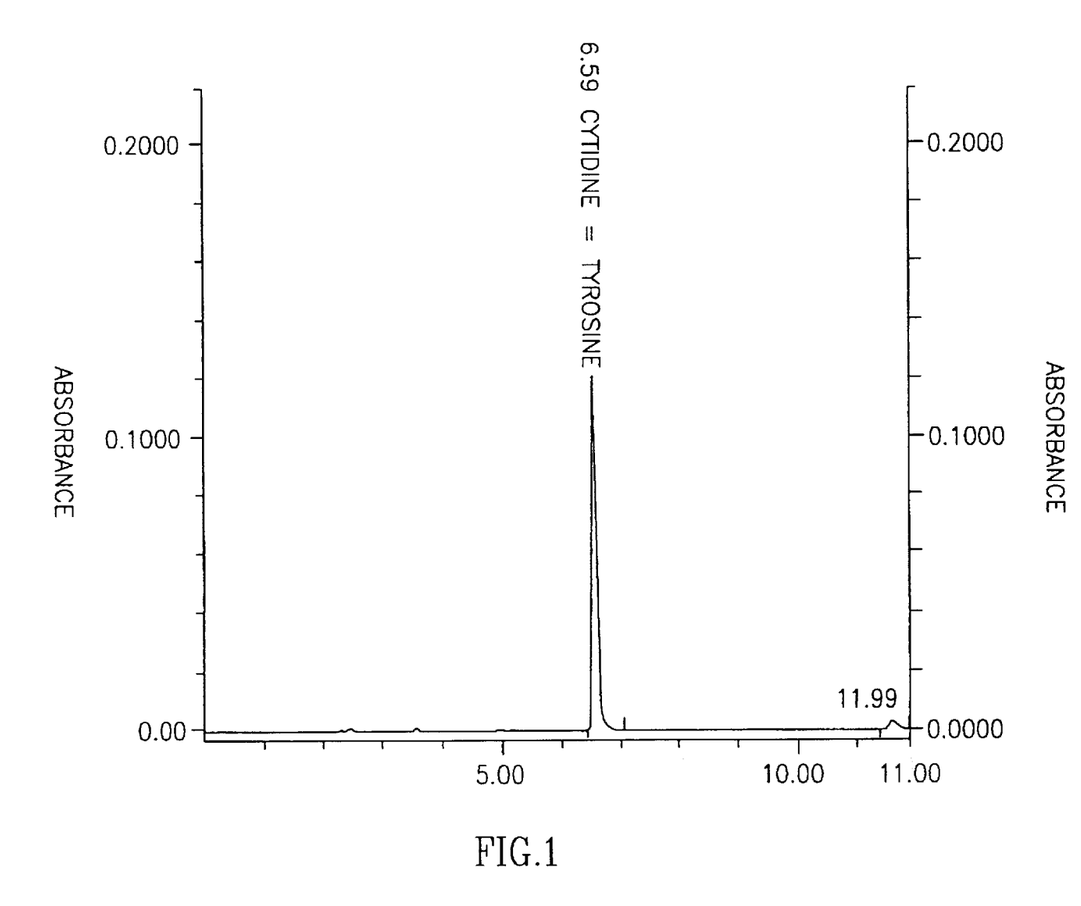
FIG. 1 illustrates the coincidence of cytidine and tyrosine peaks (6.59) when tested by a standard HPLC method.
Figure 2:
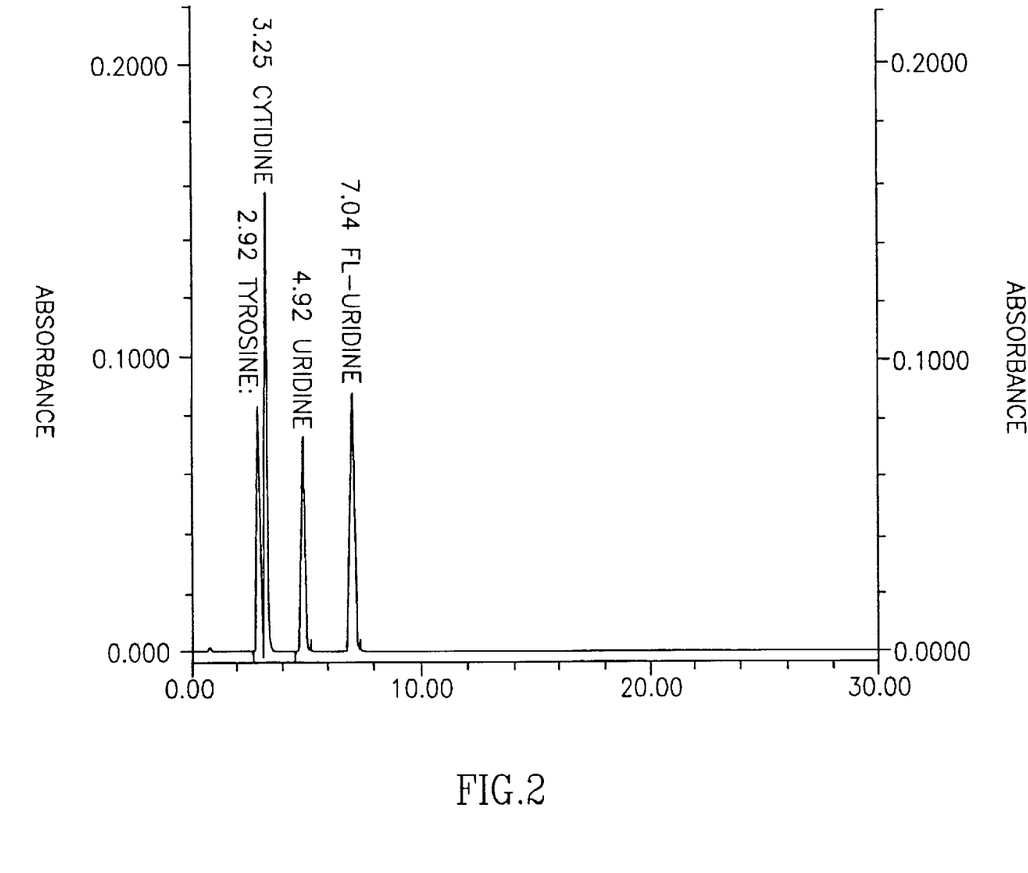
FIG. 2 illustrates distinct cytidine (3.25) and tyrosine (2.92) peaks when tested by a modified HPLC method, which utilizes elution buffer with low methanol.

In this example a new method is established that overcomes the problem of the coincidence of cytidine and tyrosine peaks when tested by a standard HPLC method for measuring various nucleosides in biological fluids (see FIG. 1). By using the standard HPLC method, one can, however, easily distinguish the uridine peak from the cytidine peak. Detailed description of the HPLC method can be found for example in Lopez-Coviella et al., (Evidence that 5'-cytidinephosphocholine can affect brain phospholipid composition by increasing choline and cytidine plasma levels. *J. Neurochemistry* 65: 889–894, 1995). Modified HPLC is carried out in a same way as standard HPLC except that elution buffer contains low amount of methanol (0.1%) instead of formic acid and as a result cytidine can be distinguished from unrelated compound tyrosine (FIG. 2). This method is useful in distinguishing cytidine from masking effect of amino acid tyrosine, which may concomitantly be present in tested biological fluid, e.g., plasma or cerebrospinal fluid (CSF). Due to the overlap between cytidine and tyrosine it is very likely that the results of all the prior art studies dealing with cytidine measurement, including present inventors' own studies supra, were interpreted incorrectly.

EXAMPLE 2

Figure 3:
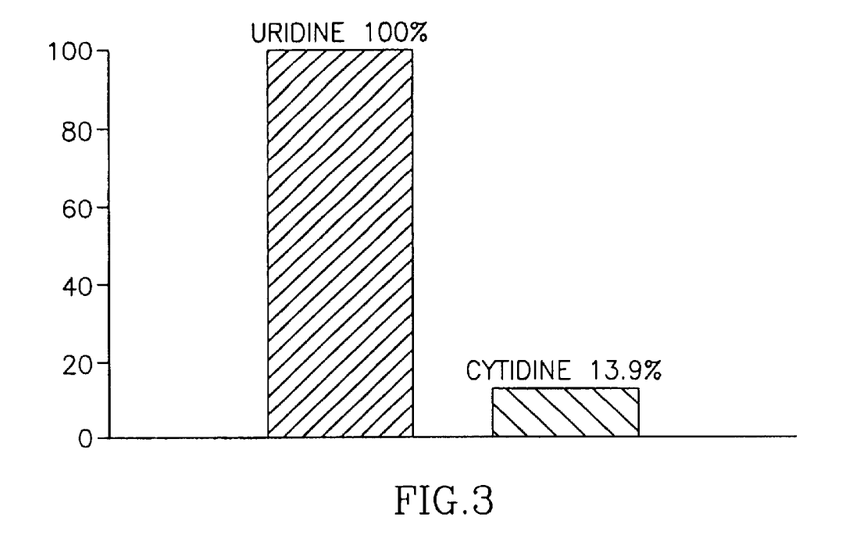
FIG. 3 shows the ratio of uridine (100%) to cytidine in plasma after oral administration of 250 milligram per kg of body weight (mg/kg) of uridine.
Figure 4:
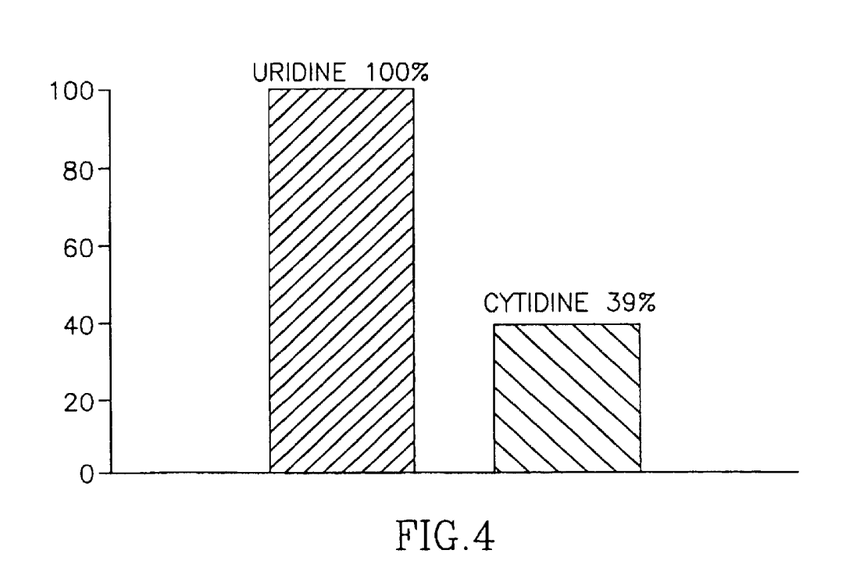
FIG. 4 shows the ratio of uridine (100%) to cytidine in the brain after oral administration of 250 milligram per kg of body weight (mg/kg) of uridine.

Gerbils, rather than rats or other rodents, are selected for this example, as the pyrimidine metabolism of said gerbils is closer to humans. For practical and ethical reasons humans cannot always be used for certain experimental studies and those skilled in the art generally recognize that the gerbil model is equivalent to a human model. Indeed, gerbils are the model of choice for certain human diseases and brain disorders such as cerebral ischemia (Ginsburg et al., Rodent models of cerebral ischemia. *Stroke* 20:1627–1642, 1989). Gerbils are given uridine orally and 60 minutes later plasma and brain levels of cytidine and uridine are measured by the modified HPLC method described in Example 1. FIG. 3 shows the relative ratio between uridine and cytidine levels in plasma after oral administration of 250 milligram per kg of body weight (mg/kg) of uridine. FIG. 4 shows the relative ratio between uridine and cytidine levels in the brain after oral administration of 250 mg/kg of undine. These results indicate that the metabolic processing of uridine in the brain is different than systemic processing of uridine in plasma. The results also indicate that uridine, when transported into the brain, is readily converted to cytidine and this conversion is more efficient in the brain than in plasma. Similar experiments are also carried out in humans wherein instead of measuring brain levels of nucleosides, the CSF levels are measured. The finding that uridine is readily converted to cytidine especially in the brain is totally unexpected and constitutes the basis for the present invention.

EXAMPLE 3

In Example 3 a clinical study is carried out with the goal of treating memory disorders and cognitive dysfunctions associated with aging as well as memory decline and cognitive dysfunction associated with pathological conditions like Alzheimer's disease, Pick's disease, Lewy Body disease, and/or dementias like Huntington's disease and AIDS dementia. Patients with non-pathological dementia associated with aging are also included. Oral doses of uridine alone ranging from 5 mg to 50,000 mg are administered daily to five male and five female patients suffering from one of the diseases listed above. The adjustment in dosage to select optimally effective pharmaceutical dose is a routine procedure well known to the practitioner skilled in the relevant art. The terms "therapeutically" or "pharmaceutically" or "pharmacologically effective dose" of a drug as used hereinafter means the amount (dosage) of the drug that provides desired clinical effect in at least 10% of treated patients" population.

Various other uridine-based compounds other than uridine itself serve as uridine source or uridine precursors. These are uridine-rich food or dietary products like algae; salts of uridine like uridine phosphates, acylated uridine or the like. These also include compounds, like CDP-choline, though structurally unrelated to uridine are able, nevertheless, to raise uridine levels in treated subjects. If required by the exigency of the therapy, therapeutically or pharmacologically effective doses of CDP-choline are also administered since it is now known that administration of said drug raises uridine but not cytidine levels and as such CDP-choline or citicoline is by definition the uridine source.

If required by the exigency of the therapy, therapeutically or pharmacologically effective doses of acyl derivatives of uridine or mixtures thereof like those disclosed in U.S. Pat. No. 5,470,838 are also administered.

If required by the exigency of the therapy, therapeutically or pharmacologically effective doses of uridine phosphorylase inhibitors like 5-benzyl barbiturate derivatives or mixtures thereof as disclosed in U.S. Pat. No. 5,141,943 are also administered.

If required by the exigency of the therapy, therapeutically or pharmacologically effective doses of uridine secretion inhibiting compounds like dilazep, hexobendine, or mixtures thereof as disclosed in U.S. Pat. No. 5,567,689 are also administered.

If required by the exigency of the therapy, therapeutically or pharmacologically effective doses of compounds which compete with uridine in kidney clearance like L-uridine, L-2',3'-dideoxyuridine, and D-2',3'-dideoxyuridine or mixtures thereof as disclosed in U.S. Pat. Nos. 5,723,449 and 5,567,689 are also administered. Therapeutically or pharmacologically effective doses of uridine as defined herein are also doses that produce blood or brain levels of cytidine ranging between 0.1 micromole ($\mu$M) and 1 millimole (mM). In general, therapeutically or pharmacologically effective doses as defined herein are also doses of drugs combination, which produce desired effect in at least 10% of treated patients=population. Doses are administered either as a single dose or divided in several doses. Drugs are administered orally such as in tablet, capsule or liquid form or parenterally by intravenous, intramuscular or subcutaneous injection.

When necessary and as required by the exigency of the therapy uridine is administered in combination with other compounds that act either synergistically or in additive manner. This reduces the therapeutic dose of administered drugs, thereby reducing potential undesirable side effects and frequency of drug administration. Compounds that act in such a manner are chemical substances participating in cholinergic metabolism. For example, compounds administered along with uridine are following choline-based compounds: choline, choline salts or esters, such as choline bitartrate or stearate or the like, or compound that dissociate to choline, such as sphingomyelin, cytidine-diphosphocholine or citicoline or CDP-choline, acylglycerophosphocholines, e.g., lecithin, lysolecithin, glycerophosphatidylcholine, mixtures thereof or the like. The choline or compound that dissociates into choline is administered so that a choline level of at least about 20–30 nanomoles and usually between 10 and 50 nanomoles is attained in patient=s blood or brain.

The pharmacologically effective doses are within about 20 mg and 50 g/day range, preferably between about 100 mg and 10 g/day. Doses are administered either as a single dose or divided in several doses, e.g., 10 mg to 1 g/cap or tab. The minimal duration of the therapy is at least one day but longer periods of time are usually required according to the exigency of the therapy. If needed, the usual time period spans from one day to the period of lifetime. When these compounds are not available in pure form the active ingredient comprises at least about 20–30 percent of the weight of the preparation. The clinical study is continued for at least 1 day or longer as required by the exigencies of the therapy. In general, the dose administered, the frequency of administration and the duration of the treatment will vary as a function of the condition of the patient and is determined according to standard clinical procedures known to the practitioner skilled in the relevant art.

EXAMPLES 4–12

In Example 4 a clinical study is carried out, which by its design and principles is similar to clinical study of Example 3 except that patients enrolled in this study are patients with cognitive dysfunction, i.e., disorders of attention, alertness, concentration, focus, and dyslexia.

In Example 5 a clinical study is carried out, which by its design and principles is similar to clinical study of Example 3 except that patients enrolled in this study are patients with mood and emotional disorders, e.g., mania, depression, stress, panic, anxiety, insomnia, dysthemia, psychosis, seasonal effective disorders and bipolar disorders.

In Example 6 a clinical study is carried out, which by its design and principles is similar to clinical study of Example 3 except that patients enrolled in this study are patients with neurological diseases like ataxias, including Friedreich's ataxia.

In Example 7 a clinical study is carried out, which by its design and principles is similar to clinical study of Example 3 except that patients enrolled in this study are patients with movement disorders like tardive dyskinesia.

In Example 8 a clinical study is carried out, which by its design and principles is similar to clinical study of Example 3 except that patients enrolled in this study are patients with strokes, cerebral thrombosis, ischemia, and related cerebrovascular diseases resulting from hypoxia.

In Example 9 a clinical study is carried out, which by its design and principles is similar to clinical study of Example 3 except that patients enrolled in this study are patients with behavioral and neurological syndromes seen after brain trauma, spinal cord injury and/or anoxia.

In Example 10 a clinical study is carried out, which by its design and principles is similar to clinical study of Example 3 except that patients enrolled in this study are patients with diseases of the peripheral nervous system, e.g., neuromuscular disorders like myasthenia gravis, the post-polio syndrome, and muscular dystrophies.

In Example 11 a clinical study is carried out, which by its design and principles is similar to clinical study of Example 3 except that patients enrolled in this study are patients with neurological diseases associated with dopaminergic pathway, e.g., schizophrenia and Parkinson's disease and said diseases are treated by combination therapy in which uridine is one of constituents.

In Example 12 a clinical study is carried out, which by its design and principles is similar to clinical study of Example 3 except that patients enrolled in this study are patients with other diseases known in the art and involving or dependent on cholinergic or uridine/cytidine metabolic pathways.

When possible clinical studies as disclosed in any preceding examples are preceded by in vivo studies in animal models, e.g., gerbil model, according to procedures established in the art.

While methods of treatment and pharmaceutical compositions recited in one of above examples have been described in detail, it will be apparent to those skilled in the art that these embodiments are exemplary rather than limiting and the true scope of the invention is that defined within the attached claims.

What is claimed is:

1. A method of increasing the level of cytidine in the brain of a subject in need thereof, comprising administering uridine or uridine-5'-monophosphate to said subject, thereby increasing the level of cytidine in the brain of said subject.

2. The method of claim 1, wherein said administering is orally administering.

3. The method of claim 1, wherein said subject is a mammal.

4. The method of claim 1, wherein said uridine is in a uridine-rich food.

5. The method of claim 1 wherein the compound administered is uridine-5'-monophosphate.

6. A method of increasing the level of cytidine in the brain of a subject in need thereof, comprising administering to said subject a pharmaceutical formulation comprising uridine or uridine-5'-monophosphate effective to increase the plasma level of uridine in said subject, thereby increasing the level of cytidine in the brain of said subject.

7. The method of claim 6, wherein said subject is a mammal.

8. The method of claim 6 wherein the formulation administered comprises uridine-5'-monophosphate.

* * * * *